US005738677A

United States Patent [19]

Colvard et al.

[11] Patent Number: 5,738,677
[45] Date of Patent: Apr. 14, 1998

[54] APPARATUS AND METHOD FOR PERFORMING EYE SURGERY

[75] Inventors: Michael Colvard, Pacific Palisades; Varouj D. Amirkhanian, Glendale; HeeJung Koh Wescoat, Garden Grove; Judy E. Mazza, El Toro; Colette Cozean, El Toro, all of Calif.

[73] Assignee: Premier Laser Systems, Inc., Irvine, Calif.

[21] Appl. No.: 455,732

[22] Filed: May 31, 1995

Related U.S. Application Data

[62] Division of Ser. No. 331,274, Oct. 28, 1994, abandoned, which is a continuation of Ser. No. 174,217, Dec. 28, 1993, abandoned, which is a continuation of Ser. No. 866,562, Apr. 10, 1992.

[51] Int. Cl.$^6$ .................................................. A61N 5/06
[52] U.S. Cl. .................. 606/4; 606/2; 606/3; 606/10; 128/898
[58] Field of Search ............... 606/2, 3-6, 10-19; 128/898

[56] References Cited

U.S. PATENT DOCUMENTS

| | | |
|---|---|---|
| 3,460,538 | 8/1969 | Armstrong. |
| 3,971,382 | 7/1976 | Krasnov. |
| 3,982,541 | 9/1976 | L'Esperance, Jr. .......... 606/14 |
| 4,024,866 | 5/1977 | Wallach. |
| 4,221,825 | 9/1980 | Guerder et al.. |
| 4,309,998 | 1/1982 | Rosa et al.. |
| 4,320,761 | 3/1982 | Haddad. |
| 4,391,275 | 7/1983 | Fankhauser et al.. |
| 4,433,692 | 2/1984 | Baba. |
| 4,501,274 | 2/1985 | Skjaerpe. |
| 4,517,973 | 5/1985 | Sunago et al.. |
| 4,517,974 | 5/1985 | Tanner. |
| 4,526,170 | 7/1985 | Tanner. |
| 4,537,193 | 8/1985 | Tanner |

(List continued on next page.)

FOREIGN PATENT DOCUMENTS

| | | |
|---|---|---|
| 0214712 | 3/1987 | European Pat. Off.. |
| 0335714 | 3/1989 | European Pat. Off.. |
| 88/03595 | 4/1989 | WIPO. |
| 90/06109 | 10/1990 | WIPO. |
| 9106271 | 10/1990 | WIPO. |
| 9117793 | 5/1991 | WIPO. |

OTHER PUBLICATIONS

The American Heritage Dictionary, 1982 p. 600.

Akopyan, V.S., et al., "New Clinical Prospects for Applying Lasers with Q-Switching in Ophthalmology", *Izvestiya Akademii Nauk SSSR, Seriya Fizicheskaya*, vol. 46, No. 10, 1982, pp. 2000–4.

Ando, Fumitaka, M.D., "Contact Lens Scalpel for Intraocular Surgery", *American Journal of Ophthalmology*, vol. 102 No. 5, Nov. 1986.

(List continued on next page.)

Primary Examiner—David M. Shay
Attorney, Agent, or Firm—Knobbe, Martens, Olson & Bear, LLP

[57] ABSTRACT

An optical probe configured for insertion into the anterior chamber of an eye, adjacent to the cataractous lens of the eye, comprises an optical source, and an optical waveguide connected to deliver optical radiation from the source to the probe. The optical radiation is in the form of pulses which have a repetition rate, a wavelength and an optical energy selected to cause significant ablation-induced damage to the lens within an ablation zone, and significant acoustic-induced damage to the lens within an acoustic zone, such that the acoustic zone is significantly larger in size than the ablation zone. The acoustic zone is created by generating shock waves which radiate from the ablation zone and propagate through hard nuclear material of the cataractous lens, such that the nuclear material is microfractured. The microfractured lens material is significantly more reactive to the laser pulses than prior to microfracturing, and the hard nuclear material readily disintegrates into small fragments in response to application of laser pulses.

6 Claims, 8 Drawing Sheets

U.S. PATENT DOCUMENTS

| | | |
|---|---|---|
| 4,538,608 | 9/1985 | L'Esperance, Jr. . |
| 4,551,129 | 11/1985 | Coleman et al. . |
| 4,558,698 | 12/1985 | O'Dell . |
| 4,559,942 | 12/1985 | Eisenberg . |
| 4,564,011 | 1/1986 | Goldman . |
| 4,582,405 | 4/1986 | Muller et al. . |
| 4,583,539 | 4/1986 | Karlin et al. . |
| 4,686,979 | 8/1987 | Gruen et al. . |
| 4,694,828 | 9/1987 | Eichenbaum . |
| 4,729,373 | 3/1988 | Peyman . |
| 4,784,135 | 11/1988 | Blum et al. . |
| 4,825,865 | 5/1989 | Zelman . |
| 4,846,172 | 7/1989 | Berlin . |
| 4,887,600 | 12/1989 | Watson et al. . |
| 4,907,586 | 3/1990 | Billie et al. ............ 606/6 |
| 4,988,163 | 1/1991 | Cohen et al. . |
| 5,041,108 | 8/1991 | Fox et al. . |
| 5,044,717 | 9/1991 | Levatter . |
| 5,071,422 | 12/1991 | Watson et al. . |
| 5,129,895 | 7/1992 | Vassiliadis et al. . |

OTHER PUBLICATIONS

Bonner, R.F., Esterwitz, Leon, et al., "Quantification of Tissue Effects due to a Pulsed Er:YAG Laser at 2.9 nm with Beam Delivery in a Wet Field via Zirconium Fluoride Fibers", SPIE, vol. 713, Optical Fibers in Medicine II, 1986.

Berlin, Michael S., M.D., et al. "Excimer Laser Photoablation in Glaucoma Filtering Surgery", American Journal of Opthalmology, May 1987.

Esterwitz, Leon, "Er:Yag Laser Shows Promise for Medical Application", 1987.

Gaasterland, Douglas E., M.D., et al., "Ab Externo Filtering Operations by Laser Contact Surgery", Ophthalmic Surgery, vol. 18, No. 4, Apr. 1987.

Goldberg, Morton F., et al. "Hisopathological Characteristics of Neodymium–Yag Laser Iridotomy in the Human Eye", British Journal of Ophthalmology, vol. 18, No. 5, May 1987.

Krasnov, Michail M., Q–Switched ("Cool") Laser in Ophthalmology, Int'l Ophthal Clinics, vol. 16, No. 4 1976, pp. 29–44.

Krasnov, M.M., "Laser Phakopuncture in the Treatment of Soft Cataracts", British Journal of Ophthalmology, vol. 59, 1975, pp. 96–98.

Karsnov, M.M., M.D., "Q–Switched Laser Goniopuncture" Arch Ophthalmol, vol. 92, Jul. 1974, pp. 37–41.

Karsnov, M.M., "Q–Switched Laser Iridectomy and Q–Switched Laser Goniopuncture", Adv. Ophthal, vol. 34, pp. 192–196, (Karger, Basel 1997).

Maguen, Ezar, M.D., et al., "Excimer Laser Ablation of the Human Lens at 308 nm wit a Fiber Delivery System", J. Cataract Refract. Surg., vol. 14, Jul. 1989.

Nanevicz, Tania M., et al., "Excimer Laser Ablation of the Lens", Arch. Ophthalmol., vol. 104, Dec. 1986.

Pellin, Michael, PhD., et al., "Endoexcimer Laser Intraocular Ablative Photodecomposition", American Journal of Ophthalmology, Apr. 1985.

Peyman, Gholam A., M.D., et al., "Effects of XeCl Excimer Laser on the Eyelid and Anterior Segment Structures", Arch. Opthalmol., vol. 104, Jan. 1986.

Puliafito, Carmen A., M.D., et al., "Excimer Laser Ablation of the Cornea and Lens, Experimental Studies", Ophthalmology, vol. 92, No. 6, Jun. 1985.

Richardson, Thomas M., M.D., et al., "Shock–Wave Effect on Anterior Segment Structures Following Experimental Neodymium: YAG Laser Iridectomy", Ophthalmology, vol. 92, No. 10, Oct. 1985.

Wheeler, C.B., "Laser Iridectomy", Phys. Med. Biol., vol. 22, No. 6, 1977, pp. 1115–1135.

Wolbarst, Myron L., "Laser Surgery; Co2 or HF", IEEE Journal of Quantum Electronics, vol. QE–20, No. 12, Dec. 1984.

van der Zypen, Eugen, M.D., "Transscleral Iridotomy Using a Neodymium: YAG Laser Operated Both with Standard Equipment and an Optical Fiber System–A Preliminary Report: Part II–Light and Electron Microscopic Findings", Ophthalmology Surgery, vol. 18, No. 5, May 1987.

Bruck, Laura B., Contributing Editor, "Special Section on Phacoemulsification", Ophthalmology Times, vol. 16, No. 10, May 15, 1992, pp. 1, 10–14, 16–17, 24, 26, 30.

Dodick, Jack M. M.D., "How Does the Nd:YAG Achieve Cataract Lysis?", Ophthalmology Times, vol. 17, No. 3, Feb. 1, 1992, pp. 1, 34–35.

Guttman, Cheryl, Contributing Editor, "First Laser Phacolysis Proves a Success", Ophthalmology Times, vol. 16, No. 21, Nov. 1, 1992, pp. 1, 12.

"First Laser Phacolysis Heralds Advances in Cataract Removal", Clinical Laser Monthly, vol. 10, No. 3, Mar. 1992, pp. 33—52.

OSN Interview, "Dodick begins term as ASCRS president", Optical Surgery News, Apr. 1, 1991, pp. 16, 19–23, 26.

H. Loertscher, W.Q. Shi, and W.S. Grundfest "Tissue Ablation Through Water with Erbium: YAG Lasers", IEEE Transactions on Biomedical Engineering, vol. 39, No. 1, Jan. 1992.

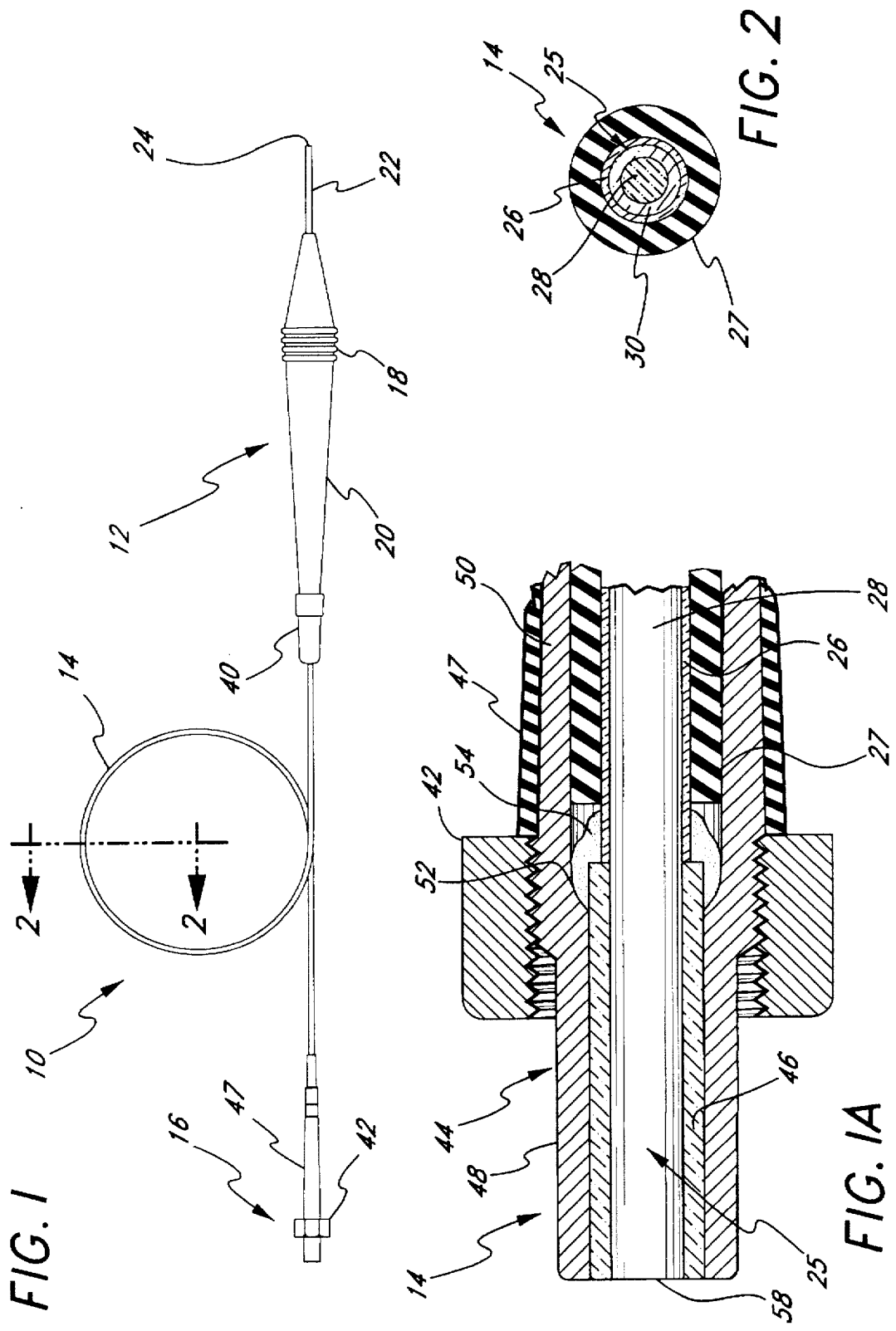

APPARATUS AND METHOD FOR PERFORMING EYE SURGERY

This application is a division of U.S. patent application Ser. No. 08/331,274, filed Oct. 28, 1994, abandoned, which is a continuation of Ser. No. 08/174,217, filed Dec. 28, 1993, abandoned, which is a continuation of Ser. No. 07/866,562, filed Apr. 10, 1992 (now abandoned).

BACKGROUND OF THE INVENTION

The present invention relates generally to the field of laser probes for surgery. More specifically, the present invention relates to laser probes used in eye surgery and to surgical techniques for treating cataracts.

Recently, attention has focused on the use of lasers to remove cataractous lens tissue by ablation, as described, for example, in U.S. Pat. No. 4,846,172 issued to Berlin. Although soft tissues are relatively easy to ablate, the nucleus of a cataractous lens is quite hard, and thus ablation of such nucleus material is time consuming and tedious. In order increase the speed of the photoablative process, the power of the laser may be increased. However, such high power increases the risk of thermal damage, particularly the chances of rupturing the posterior capsule of the eye and of causing other damage to the surrounding eye tissues.

In other cataract surgeries, various types of ultrasonic devices are used to remove the lens. Typically, ultrasonic energy is directed against the lens of the eye to separate the lens into large pieces which must be continuously broken down into smaller pieces before they can be removed. In many prior art ultrasonic probes, aspiration is provided through a coaxial aspiration port to attract large lens pieces to surface of the ultrasonic probe, and hold the lens pieces in place, so they can be broken down into smaller pieces by the ultrasonic waves. This process of attracting, and breaking the pieces of the lens is repeated until the pieces are small enough to fit through the aspiration port in the ultrasonic probe. The process of separating the lens into pieces, and breaking the pieces into smaller pieces requires a high level of skill and is also very time consuming. Therefore an improved lens removal procedure is needed.

SUMMARY OF THE INVENTION

In accordance with one aspect of the present invention, cataractous lens tissue, including hard nuclear material, is emulsified by means of a laser operating in a unique pulsed regime which simultaneously produces an acoustic (i.e., photo acoustic) effect and an ablative effect on the lens tissue. The ablative effect is limited to an ablation zone which generally corresponds in size to the diameter of the laser beam spot (typically no more than about 300 microns). As laser pulses ablate the lens tissue, microscopic particles of tissue are dislodged, and if a sufficient number of pulses are directed on a particular location, the ablation will form a crater at that location. In contrast to the ablation effect, the acoustic effect is less confined. Acoustic energy, in the form of shock waves generated during ablation by the pulsed laser energy, radiate beyond the ablation zone throughout an acoustic zone which may be many times the size of the ablation zone. These shock waves create microfractures in the lens tissue, and effectively weaken the structure of the lens tissue, particularly the hard nuclear material. The microfractured tissue is significantly more reactive to the laser pulses than tissue which has not been microfractured. As the laser beam spot is passed repeatedly across the lens tissue, the microfractured lens tissue readily disintegrates into small fragments. At the same time, ablation erodes the lens tissue, resulting in a viscous milky fluid. The milky fluid and small fragments mix during the process to form an emulsion which generally may be easily aspirated through an aspiration tube having a diameter of about 500 microns or less (as used herein, the term "emulsion" includes a substantially fluid suspension).

In the present invention, a laser surgery apparatus is used to perform the above-discussed phacoemulsification process. The apparatus comprises an optical probe configured for insertion into the anterior chamber of an eye adjacent to the lens of the eye. An optical waveguide, connected to the probe, delivers optical radiation through the probe to the lens. An optical source produces the optical radiation in the form of pulses. These pulses are at a repetition rate, wavelength and an optical energy selected to cause significant ablation-induced damage to the lens within an ablation zone, and significant acoustic-induced damage to the lens within an acoustic zone, with the acoustic zone being significantly larger in size than the ablation zone. The pulses preferably have a repetition rate of 5–25 pulses per second, with an energy per pulse of 10–80 mJ and an energy density of about 35–70 J/cm$^2$. In the preferred embodiment, the repetition rate is about 10 pulses per second, the energy per pulse is about 35 mJ, and the energy density is about 45 J/cm$^2$. The wavelength of the optical radiation is preferably in the infrared region of the optical spectrum, and may be 2.94 microns, as produced by an Er:YAG laser.

A further aspect of the invention includes a method of removing a lens of an eye. A probe is inserted into the anterior chamber of the eye, and pulses of laser radiation from the probe are directed onto nuclear material of the lens. The wavelength, repetition rate and pulse energy of the laser radiation simultaneously ablate the lens within an ablation zone and generate shock waves which radiate from the location and propagate through the nuclear material to acoustically damage nuclear material within an acoustic zone that extends outside the ablation zone. The probe is moved such that the pulses of laser radiation are directed onto acoustically damaged material, whereby simultaneous ablation and shock wave generation readily transform the nuclear material into an emulsion. The method also includes aspirating the emulsion from the eye.

Yet another aspect of the invention comprises a method of removing the lens of an eye in which lens tissue is microfractured by directing laser pulses onto the lens such that the lens is significantly more reactive to the pulses than prior to the microfracturing. Pulses are then directed onto the microfractured lens tissue. In the preferred method, the pulses directed onto the microfractured tissue have the same pulse parameters as the pulses used to microfracture the lens tissue.

Still another aspect of the invention involves a method of removing a lens of an eye by inserting an elongated laser probe through a primary incision in the eye, into the anterior chamber of the eye. A tip of the probe is positioned in proximity to the lens. Pulsed laser radiation is supplied to the probe, and the laser radiation is directed from the tip along a path to a location on the lens to emulsify lens tissue. An elongated aspiration probe is inserted through a side port incision in the eye, into the anterior chamber of the eye. A tip of the aspiration probe is positioned in proximity to the aforementioned location without occluding the pulsed laser radiation. Emulsified lens tissue is removed from the path of the laser radiation by drawing the lens tissue through the aspiration probe in a direction transverse to the path. Preferably, the aspiration probe is used to mechanically stabilize the eye and prevent movement thereof while the pulsed laser radiation is directed on the aforesaid location. In the preferred method, the aspiration probe is also used to manipulate intraocular tissue while the pulsed laser radiation is directed at such location. After the method has been completed, both probes may be removed from the eye, and the aspiration probe may be inserted through the primary incision so as to retrieve small pieces of ablated or emulsified material from all "o'clock" positions within the anterior chamber of the eye, and to remove soft cortical remnants of cataract tissue, as well as to vacuum the internal surface of the lens capsule.

A further aspect of the invention involves an apparatus for removing a cataractous lens of an eye which comprises an elongated laser probe, configured for insertion into an anterior chamber of the eye. The probe comprises a focusing lens which is connected to a source of pulse laser energy. The focusing lens tightly focuses the laser energy to provide an energy density at a focal spot of at least tens of Joules per square centimeter. The tight focusing causes the focal spot to be proximal to an output surface of the focusing lens, whereby the energy density rapidly decreases beyond the focal spot to avoid damage to the posterior capsule of the eye during removal of the lens. The pulse laser energy has a repetition rate of about 5 to 25 pulses per second. The repetition rate at the aforementioned energy density generates shock waves which radiate outwardly from the focal spot into nuclear cataractous lens tissue at an acoustic intensity sufficient to cause substantial acoustic damage to the nuclear cataractous lens tissue. In the preferred embodiment, the focusing lens is the forwardmost portion of the probe to permit the focusing lens to be placed directly against the cataractous lens. The focal spot is about 1½ mm or less from the output surface of the lens, and the energy density at the focal spot is at least 35 Joules per square centimeter.

BRIEF DESCRIPTION OF THE DRAWINGS

FIG. 1 is a diagram of a laser delivery apparatus used with the probe of the present invention.

FIG. 1A is an enlarged view in partial cross section of the laser coupling assembly of FIG. 1.

FIG. 2 is a cross-sectional view of an optical waveguide used with probe of the present invention, surrounded by a protective jacket.

DETAILED DESCRIPTION OF THE INVENTION

The present invention comprises an improved laser probe for eye surgery and improved surgical methods relating to emulsification of a cataractous lens.

Figure 4:
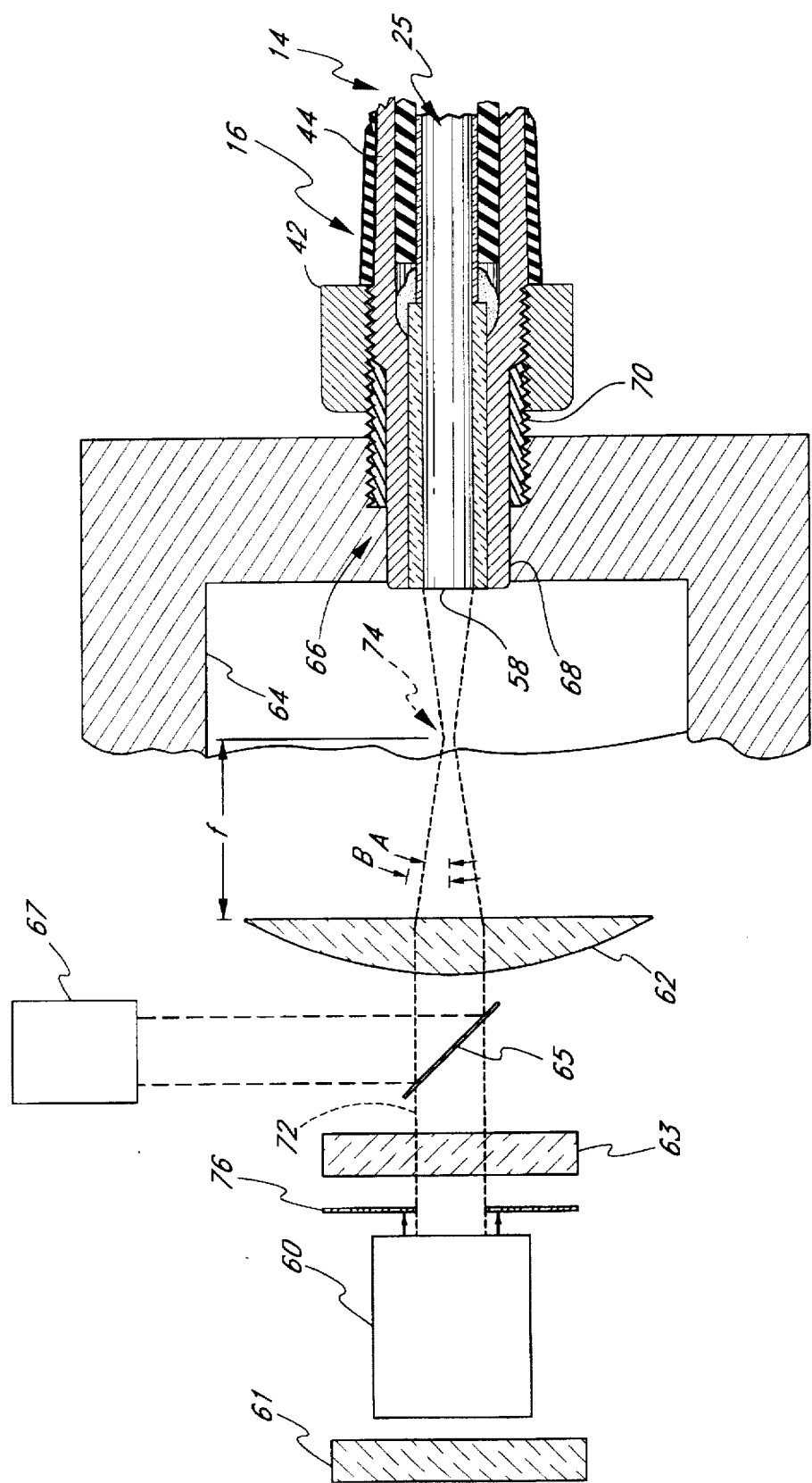
FIG. 4 is a diagram of a laser coupled to the coupling assembly of FIG. 1A.

As shown in FIGS. 1 and 2, a medical laser delivery system 10 comprises a handpiece 12, an optical waveguide 14 and an input coupling assembly 16 for attaching the waveguide 14 to a laser 17 (shown in FIG. 4). The handpiece 12 has larger diameter than the waveguide 14 and is shaped so that it is easily manipulated by the hand of a user. The hand piece 12 may possess ridges 18 on its exterior to secure a person's grip on the handpiece 12. The handpiece 12 comprises a body portion 20, sized for grasping by the hand of a user, and a guide portion 22 which projects distally therefrom. The guide portion 22 comprises a stainless steel tube through which a distal portion 24 of the waveguide 14 extends, and the guide portion 22 functions to provide rigidity to the distal end 24 of the waveguide 14. The distal end of the guide portion 22 may be attached to a threaded housing so as to allow different embodiments of the improved laser probe of the present invention or other types of tips to be attached to the handpiece 12.

A cross-sectional view of the optical waveguide 14 is illustrated in FIG. 2. Preferably, the overall length of the waveguide 14 is about one meter. The waveguide 14 comprises a guiding structure 25 surrounded by a protective structure 26. Optionally, the protective structure 26 may be covered by an outer flexible sleeve or jacket 27. The guiding structure 25 comprises a multimode optical fiber having an inner core 28 and an outer cladding 30. The core 28 and cladding 30 are made of a fluoride-based material such a zirconium fluoride, aluminum fluoride, or hafnium fluoride. The core 28 and cladding 30 are fluoride doped with impurities such that the cladding 30 has a lower index of refraction than the core 28. Desirably, the refractive index of the core 28 is 1.511 and the refractive index of the cladding 30 is 1.497. The guiding structure is manufactured using conventional optical fiber manufacturing techniques which are well known in the art.

Preferably, the protective structure 26 of the laser delivery system comprises a buffer material which is highly transmissive to infrared light, sufficiently strong to protect the fiber against breakage, flexible and moisture resistant. The preferred buffer material comprises a layer of thermoplastic polyimide having a thickness of 0.01 mm (such as Pyralin™, available from DuPont). The polyimide comprises linear polymers having generally the imide group—CONCO—as part of the polymer chain. The polyimide buffer material surrounds and is bonded to the cladding 30 using conventional techniques. Polyimide has a glass transition temperature of about 340° C., a tensile strength of about 19,000 psi, a thermal conductivity of about 0.00035 cal/(cm)(sec)(° C.), and an index of refraction of about 1.7 (e.g., 1.623). It has been found that, when used as a buffer for a fluoride-based fiber, polyimide dramatically increases the power handling capability of the fiber such that sustained transmission of infrared light having a wavelength of about 3 microns is possible at a power density of at least 4 kW/cm$^2$ over a fiber length of about 1 to 3 meters. In effect, the polyimide dissipates the energy from leaky modes of the fiber without creating hot spots which could damage the fiber. The outer jacket 28, if used, may comprise PVC, polysulfone or other tubing material. The jacket 28 is sized to fit over the protective structure 26 and slides thereon without being bonded thereto.

Figure 3:
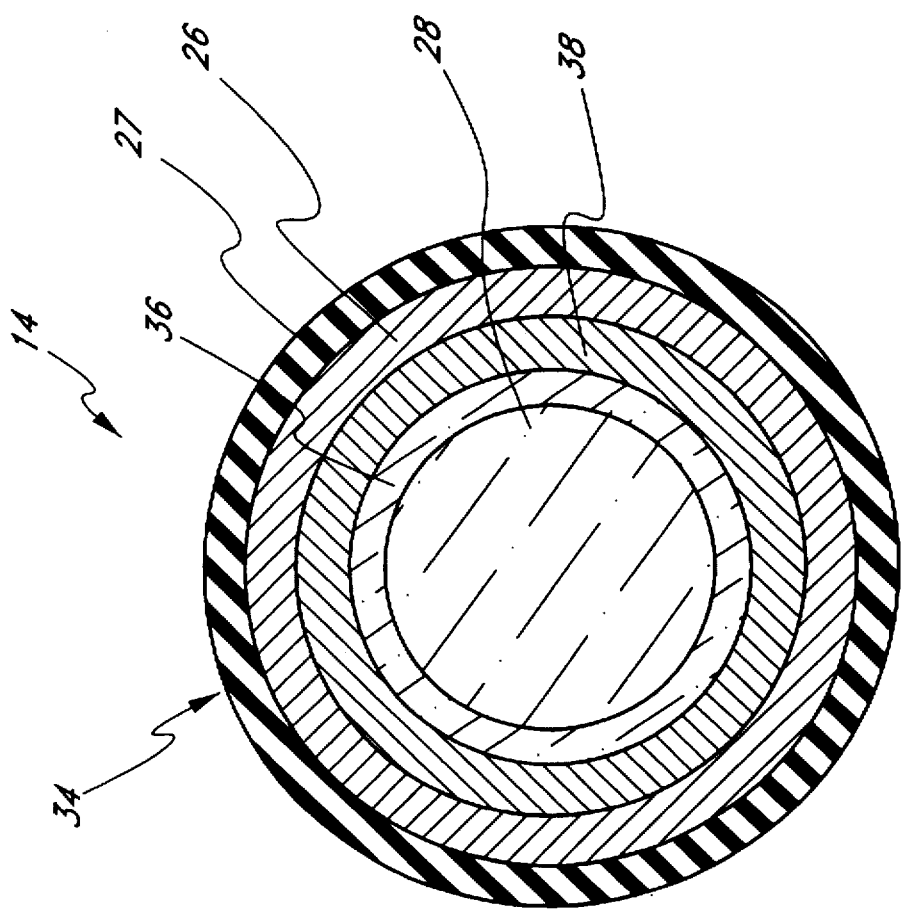
FIG. 3 is a cross-sectional view of an alternate embodiment of the optical waveguide, surrounded by a protective jacket.

A cross-sectional view of an alternative embodiment of the optical waveguide 14 is illustrated in FIG. 3. The alternative embodiment comprises a double clad fiber 34 which comprises the core 28, surrounded by an inner cladding 36, which in turn is surrounded by an outer cladding 38. The double clad fiber 34 is surrounded by the protective structure 26 and the jacket 28. The protective structure 26 of the preferred embodiment comprises a layer of polyimide material, as described above, that has an index of refraction, higher than that of the claddings 36, 38. The outer cladding 38 is provided to inhibit light propagating in leaky modes of the inner cladding 36 from reaching the polyimide protective structure 26, and the outer cladding 38 has a lower index of refraction than the inner cladding 36 for this purpose. Most of the light in the inner cladding 36 will thus be guided within the inner cladding 36 due to the fact that the index of refraction for the inner cladding 36 is higher than that of the outer cladding 38. Accordingly, by adding an extra layer of cladding, light leaking out of the core 28 is advantageously kept within the inner cladding 36 to decrease the amount of energy reaching the protective structure through leaky modes.

Referring back to FIG. 1, the optical waveguide 14 extends through the center of the handpiece 12 and emerges at the distal end 24, creating a path for laser light to travel through the handpiece 12 and out the distal end 24 to the tissue site T. The waveguide 14 is protected from breakage at the point of entry to the handpiece 12 by a strain relief 40. The strain relief is preferably made of PVC tubing.

A cross-sectional view of the input coupling assembly 16 is shown in FIG. 1A. The coupling assembly 16 comprises a lock nut 42, a male fitting 44, a tubular sleeve 46 of IR grade silica and a strain relief 47. Both the male fitting 44 and the lock nut 42 are made of stainless steel (i.e., an SMA-905 connector). The male fitting 44 comprises a narrow tubular proximal end portion 48 which has a smaller diameter than a tubular distal portion 50. The exterior of the wider distal portion 50 is partially threaded so that the lock nut 42 may be screwed over it. The inner diameter of the distal portion 50 of the fitting is approximately equal to the diameter of the waveguide 14 (including any outer jacket 28).

The sleeve 46 is located within the inner diameter of the narrow proximal end 48 of the mare fitting 44, and has a wall thickness which may be about 300% of the cladding thickness. The outer diameter of the sleeve 46 is equal to the inner diameter of the fitting 44 in the proximal end portion 48. However, in the wide portion 50, the inner diameter of the fitting 44 becomes larger, leaving a recess 52 between the tubing 46 and the inner wall of the fitting 44. A proximal end portion of the waveguide 14 is inserted into the sleeve 46. This portion has the jacket 28 (FIG. 2) and the polyimide buffer 26 removed, leaving only the guiding structure 25. The buffer 26 terminates at the inner end of the sleeve 46. The guiding structure 25 is inserted within the sleeve 46, and the sleeve 46 is sized so that the guiding structure 25 is flush against the inner wall of the quartz sleeve 46 without intervening material such that it is not bonded to the sleeve 46. The waveguide 14 is fastened to the sleeve 46 by epoxy glue 54 which is placed in the recess 42 between the inner wall of the fitting 44 and the waveguide 14. A proximal end 58 of the waveguide 14 is cleaved or dry-polished with the sleeve 46 mounted thereon so that the input face formed by the sleeve and guiding structure is sufficiently smooth to prevent significant scattering of light as it enters the waveguide. The polishing is accomplished using 9 micron, 5 micron and 0.3 micron polishing paper. Preferably, the polishing is accomplished "dry," without water or by oil base polishing, since fluoride-based fibers have an affinity for water.

FIG. 4 illustrates the attachment of the coupling assembly 16 of the waveguide 14 to the laser 17. The laser 17 comprises an infrared lasing medium 60 (e.g. a solid rod of Er:YAG) disposed between a rear reflector 61 and a front output coupler 63. The reflector 61 reflects 99.5% of the light incident thereon while the output coupler 63 reflects about 90% of the light incident thereon to form a laser cavity. A beam combiner 65, such as a dichromic mirror, is placed just outside the laser cavity to combine the invisible laser beam from the Er:YAG laser 17 with a visible aiming beam from a Helium Neon (HeNe) laser 67. The beam combiner 65 transmits substantially all of the laser energy from the laser cavity and reflects substantially all of the energy from the HeNe laser 67 to form an output beam which is directed to a plano-convex focusing lens 62. The HeNe laser 67 is within the visible spectrum and is used as an aiming beam to determine the location of the invisible infrared laser energy. The focusing lens 62 focuses light from the beam combiner 65 for input to the coupling assembly 16. The laser medium 60 and the lens 62 are contained within a chassis 64. The chassis 64 has a female fitting 66 comprising a hole 68 having a slightly larger diameter than the narrow end 48 of the male fitting 44 to enable insertion of the narrow end 48 into the hole 68, and a threaded sleeve 70 having an inner diameter slightly larger than that of the hole 68, and an outer diameter sized to receive the lock nut 42 (FIG. 1A). The narrow end 48 of the male fitting 44 is inserted into the hole 68, and the lock nut 42 is screwed onto the sleeve 70, thereby securing the male fitting 44 to the chassis 64. The axial length of the sleeve 70 and thickness of the chassis 64 are such that the proximal end 58 of the waveguide 14 projects slightly past the interior surface of the chassis 64.

The laser cavity emits a laser beam 72 which propagates through the beam combiner 65 and combines with the beam from the HeNe laser 67. The combined beam is transferred to the lens 62 and is focused at a focal point 74. The end 58 of the optical waveguide 14 is located just past the focal length f of the lens. The focusing of the laser beam 72 will produce a small beam spot on the end 58 of the waveguide 14. It is desirable that the laser beam's spot diameter be incident within 80% of core 28 to minimize the amount of the laser light incident on the sleeve 46 of the coupling 16. The positioning of the waveguide 14 in relation to the focal length f of the lens is important to insure that the infrared laser beam spot be incident within 80% of the core 28. As is well known, the diameter of the beam spot at the focal point 74 is a function of the focal length f of the lens 62 and the divergence angle of the laser beam 72. One embodiment of the invention uses a lens with a 15 mm focal length f. The energy distribution within the spot is a function of the modes of the laser cavity. The $TEM_{00}$ mode of the laser cavity is the lowest order mode. It has an intensity distribution which follows a gaussian curve so that the peak energy is located at the center of the beam. The $TEM_{00}$ mode is therefore desirable because it produces maximum intensity at the center of the beam spot. In order to limit the output of the multimode laser cavity to the $TEM_{00}$ mode, a restricting aperture 76 is placed in the path of the beam 72 inside the laser cavity between the laser medium 60 and the output coupler 63.

It is also desirable to keep the focused optical energy within the numerical aperture of the guiding structure 25. The numerical aperture (N.A.) of the guiding structure for the $TEM_{00}$ mode is the sine of the maximum acceptance half angle within which light entering the core 28 will undergo total internal reflection and therefore remain within the core 28. The N.A. of the fiber is found by the equation:

$$N.A. = \sqrt{n_1^2 - n_2^2}$$

where $n_1$ is the refractive index of the core 28 and $n_2$ is the refractive index of the cladding 30. The N.A. of the laser beam 72 entering the core 28 is equal to the beam diameter before entering the lens 62 divided by twice the focal length of the lens. To reduce losses and heat damage, it is preferable that the numerical aperture of the waveguide 14 be greater than the numerical aperture of the beam 72; or stated another way, that the convergence angle A of the beam 72 be less than the acceptance angle B of the waveguide 14. The restricting aperture 76 additionally serves to reduce beam divergence and to keep the beam diameter within the limits needed to produce a numerical aperture within that of the guiding structure 25.

During operation, the multimode laser beam 72 is restricted by the aperture 76 to produce the $TEM_{00}$ mode, and focused by the lens 62 onto the end 58 of the fiber core 28 (FIG. 2). The light travels through the waveguide 14 to the distal end 24 where it may be further focused by a lens 62 or directly transmitted to the tissue site. The physician performing a surgical operation holds the handpiece 12 to direct the laser beam 72 to the desired target location T. The waveguide 14 is capable of transmitting light having high power densities, at least 4 kilowatts per square centimeter at a wavelength of about 3.0 microns (2.94 µm for Er:YAG). The laser 17 is a pulsed Er:YAG laser which produces pulses having a pulse duration of 250 µsec to 300 µsec. Each pulse is comprised of a train or burst of sub-pulses, each having a duration of about 200 nsec.

Figure 5:
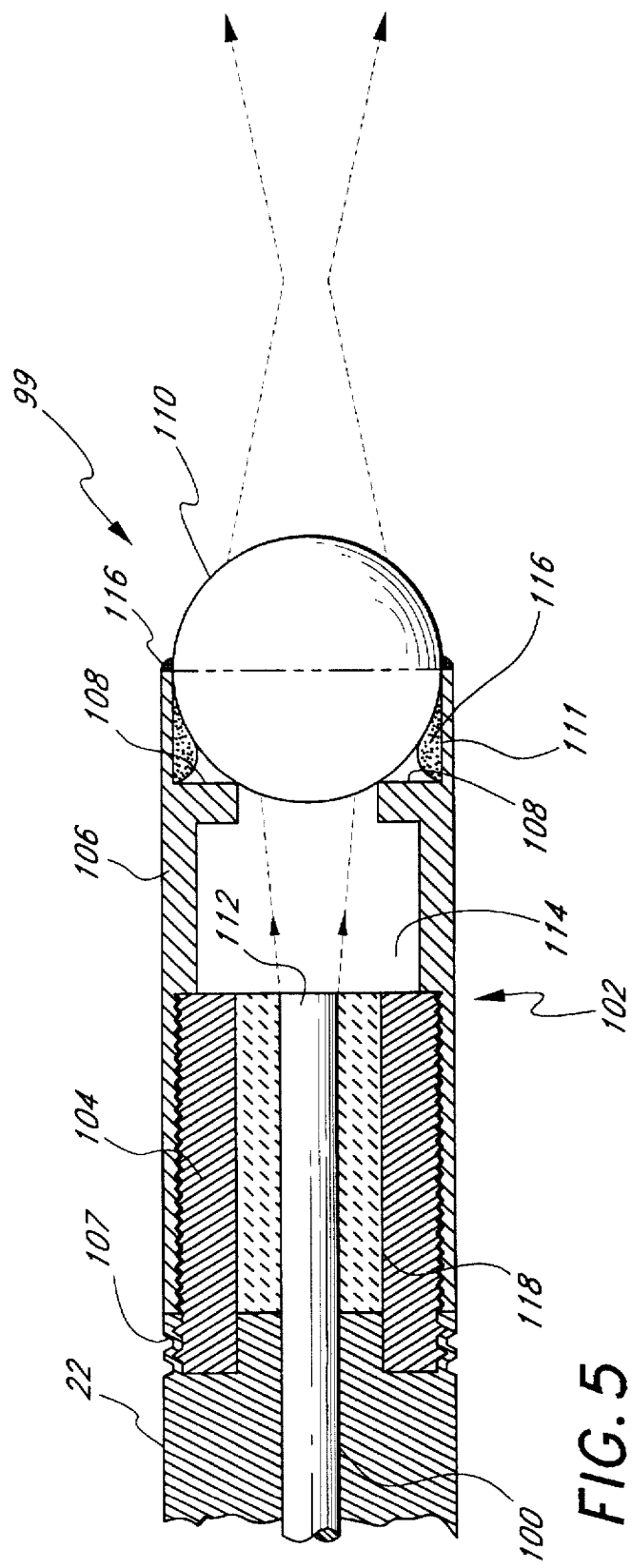
FIG. 5 is a view in partial cross section of one embodiment of the probe of the present invention which utilizes a micro-ball lens.

The laser energy from the medical laser delivery system described above is delivered to the improved laser probe of the present invention. Referring to FIG. 5, one embodiment of the laser probe 99 of the present invention is illustrated. In this embodiment, a small lens system, such as a micro-ball lens having a short focal length, is used to focus the laser energy to deliver the precise small spot diameter of high density laser energy. The waveguide 14 in this embodiment comprises a fluoride based optical fiber 100 which extends from the laser source 17 to the handpiece 12 of the laser delivery system described above (FIGS. 1–4), and exits the guide portion 22. The guide portion 22 for example may be formed of a piece of stainless steel tubing, henceforth referred to as hypo-tubing. A brass ferule housing 102 is used to attach the laser probe 99 to the guide portion 22. The brass ferule housing 102 comprises a proximal portion 104 and a distal portion 106. The proximal portion 104 is threaded into the distal portion 106 to attach the two pieces. The proximal portion 104 of the brass ferule housing 102 is placed inside the distal end 24 of the guide portion 22 and the two pieces are attached together at a crimp 107 using conventional crimping techniques. The proximal portion 104 of the brass ferule housing 102 maintains the alignment of the fluoride fiber 100 within the brass ferule housing 102 using a fiber alignment sleeve 118. The distal portion 106 of the brass ferule housing 102 comprises a hemispherical lens holder 108 which comprises stops designed to position and hold a micro-ball lens 110. The micro-ball lens 110 is preferably a sapphire lens, an IR Quartz ball lens or a silica micro-sphere. In this embodiment 99, the laser energy from the fluoride fiber 100 will be transmitted from the exposed end 112 of the fluoride fiber 100 through an air gap 114 of 1 mm within the brass ferule housing 102 to the micro-ball lens 110 where it is focused to the desired spot size before transmission out of the probe 99. The micro-ball lens 110 is epoxied into place in the hemispherical lens holder 108 against the stops using U.V. cured or 5 minute epoxy 116 to fill in the space between the micro-ball lens 110 and the walls 111 of the hemispherical lens holder 108. The proximal portion 104 of the brass ferule housing 102 is threaded into the distal portion 106 of the brass ferule housing 102, thereby aligning the micro-ball lens 110 with the fluoride fiber 100. An airtight sealing of both portions of the brass housing 102 is maintained to prevent fluid or other debris from leaking into the housing 102 and damaging the fluoride fiber 100 or blocking the path of the laser energy.

Figure 6:
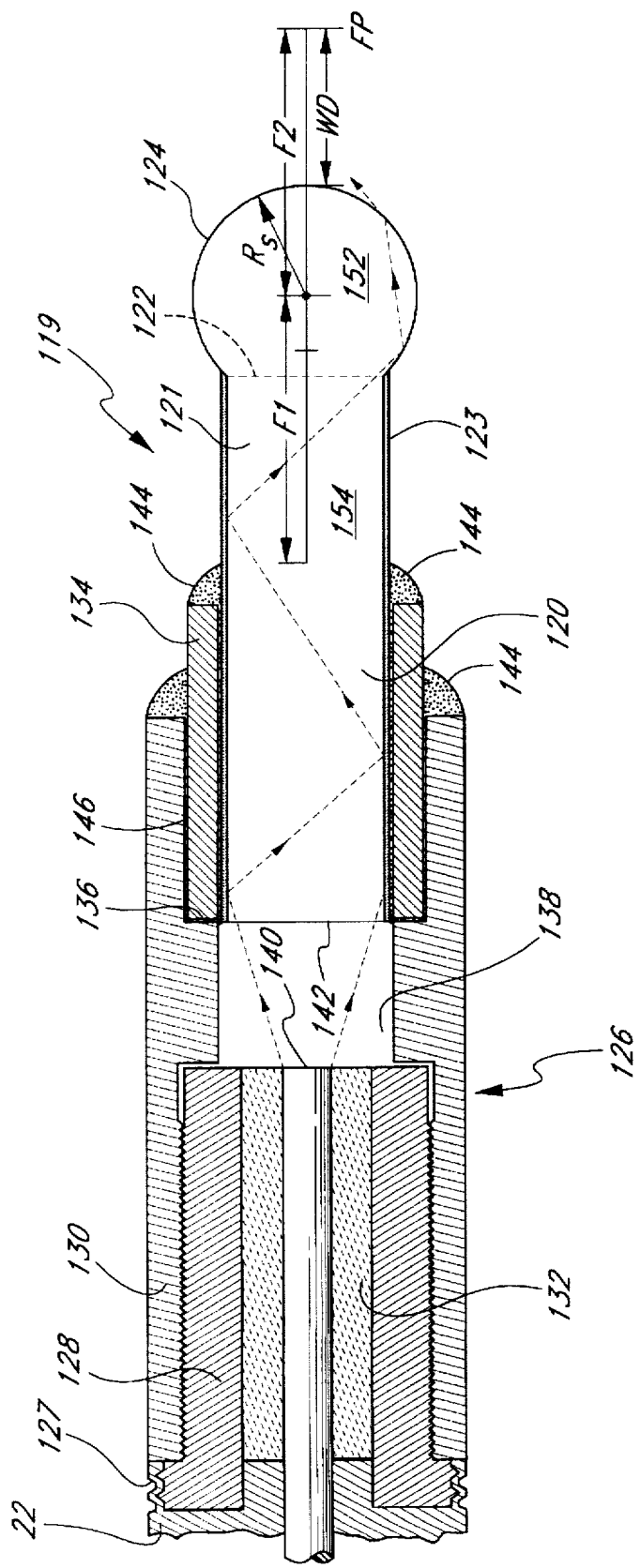
FIG. 6 is a view in partial cross section of another embodiment of the probe of the present invention which utilizes a silica fiber pigtail having an end formed in the shape of a micro-ball lens.

In another embodiment of the probe of the present invention, illustrated in FIG. 6 as the probe 119, a short fiber 120 is connected to one end of the fluoride based fiber 100. As noted above, the fluoride based fiber 100 is preferred for transmitting IR laser energy with an approximate wavelength of 3 microns, such as Er:YAG laser energy, over long distances. However, the fluoride fiber 100 is toxic and has a low melting temperature which causes the fluoride fiber 100 to melt when it comes into contact with lased tissue debris. In contrast, the fiber 120 is comprised of non-toxic material which and has a high melting point, such as low OH silica having a low water content (e.g., 1–2 ppm) or sapphire. The preferred embodiment comprises a short silica pigtail 120 which is positioned at the end of a fluoride based optical fiber 100 to provide the delivery of the IR laser energy to the desired internal target of the eye. A distal end 122 of the silica fiber 120 is melted to form a micro-ball shaped surface 124 to focus the laser energy to the desired small spot size. In this embodiment of the laser probe of the present invention, a 0.2 N.A. fluoride based optical fiber with a 200–400 µm diameter core 28 (FIG. 2) is used to deliver the laser energy. Preferably, a 400 µm diameter core 28 is used. The fiber pigtail 120 comprises a silica low-OH 0.2 N.A. optical fiber with a 500–1500 µm diameter core 121. Preferably, the silica fiber has a 800–1000 µm diameter core 121 surrounded by a 40–50 µm thick cladding layer 123 on all sides, which is easily optically coupled to the preferred 400 µm diameter core 28 of the fluoride fiber 100.

A brass ferule housing 126, similar to the housing described above, is used to align the silica fiber pigtail 120 with the fluoride fiber 100. The brass ferule housing 126 comprises two pieces which are threaded together to align the two fibers, a first proximal piece 128 and a second distal piece 130. The proximal piece 128 of the brass ferule housing 126 is threaded into the distal piece 130 to align the fibers. The proximal piece 128 of the brass ferule housing 126 is placed within the distal end 24 of the guide portion 22 of the handpiece 12 (FIG. 1), and the two pieces are attached together at a crimp 127 using conventional crimping techniques. The guide portion 22, such as a piece of hypo-tubing, guides the fluoride fiber 100 into the brass ferule housing 126 and maintains the position of the fluoride fiber 100 with respect to the handpiece 12. Within the proximal piece 128 of the housing 126, the fluoride fiber 100 is placed in a fiber alignment sleeve 132, such as a piece of quartz tubing, to position the fluoride fiber 100 with respect to the silica fiber pig tail 120. In the distal piece 130 of the brass housing 126, the silica fiber pigtail 120 is encased within a separate positioning structure 134, i.e. a piece of hypo-tubing. The positioning structure 134 abuts a positioning flange 136 inside the distal piece 130 of the brass ferule housing 126, and extends along the length of the silica fiber pigtail 120 before terminating proximal to the micro-ball shaped surface 124 of the silica pigtail 120. The positioned structure 134 protects and supports the silica fiber 120 as it extends from the distal piece 130 of the brass ferule housing 126. Preferably, when the two pieces 128, 130 of the brass ferule housing 126 are assembled by threading the distal piece 130 onto the proximal piece 128, the silica fiber pigtail 120 and fluoride fiber 100 are positioned to allow for a 1 mm air gap 138 between a distal end 140 of the fluoride fiber 100 and a proximal end 142 of the silica fiber pigtail 120 within the brass ferule housing 126. The air gap 138 is provided to prevent the distal end 140 of the fluoride fiber 100 from breaking down over long periods of continuous lasing, approximately 2–7 minutes in duration at high pulse repetition rates. As mentioned above, the fluoride fiber 100 has a low melting temperature caused by its low glass transition temperature Tg, therefore it can not withstand elevated temperatures for long periods of time. The silica fiber pigtail 120 is capable of transmitting up to 80% of the output laser energy from the fluoride fiber 100, and the remaining 20% or more of the energy is reflected, refracted and absorbed. The energy that is absorbed by the fibers 100, 120 eventually is converted into heat. The accumulation of excessive heat at the distal end 140 of the fluoride fiber 100 can cause the breakdown of the fluoride fiber 100. The preferred 1 mm air gap 138 between the fluoride fiber 100 and the silica fiber pigtail 120 was chosen to reduce heat damage of the fluoride fiber 100 while still enabling the coupling of the fluoride fiber 100 with the preferred 400 μm diameter core 28 with the silica fiber pigtail 120 with the preferred 800–1000 μm diameter core 121, both fibers with a 0.2 N.A. acceptance angle. Further, the proximal or input end 142 of the silica fiber pigtail 120 is preferably covered with an anti-reflective coating, such as $MgF_2$ at 2.94 microns, to minimize the amount of energy that is reflected from the proximal end 142 of the silica fiber pigtail 120 to the distal end 140 of the fluoride fiber 100, thereby further reducing the damage to the fluoride fiber 100.

The silica fiber pigtail 120 is manufactured by cutting a low-OH silica fiber using a fiber cleaver to 10–15 mm in length. Both ends of the cut fiber are successively polished with 15, 9, 3, and 0.3 μm polishing papers. Next, the U.V. acrylate jacket 27 is removed from the entire length of the silica fiber. The support structure 134, such as hypotubing, is attached to the silica fiber 120 using epoxy 144 In turn, the support structure 134 with the silica fiber 120 enclosed is attached to a wall 146 of the distal piece 130 of the brass ferule housing 126 using epoxy 144 to prevent any fluid or debris from entering the housing 126. The establishment of a watertight seal around the brass ferule housing 126 is especially important as water will damage the fluoride fiber 100. Finally, the distal end 122 of the silica fiber 120 is fused, or melted, by a fusion splicer to create the proper configuration of the micro-ball surface 124. The radius of the micro-ball surface 124 is controlled by the amount of current applied by the fusion splicer as well as the duration of exposure to the current of the fusion splicer. The radius and the position of the focal point 150 of the micro-ball surface 124 of the silica fiber pigtail 120 is calculated using Paraxial theory $$F1 = Rs\ n1/(n2-n1)$$

$$F2 = Rs\ n2/(n2-n1)$$

where F1, the focal length of the probe, is the distance from the center 152 of the micro ball 124 to the focal point 150 in a medium with a refractive index n1 (i.e., the focal length of the micro-ball lens). F2 is the distance from a proximal focal point 154 to the center 152 of the micro-ball 24, n2 is the refractive index of the micro-ball, and Rs is the radius of the micro-ball 124. These parameters are preferably selected to yield a relatively short focal length F1.

Figure 7:
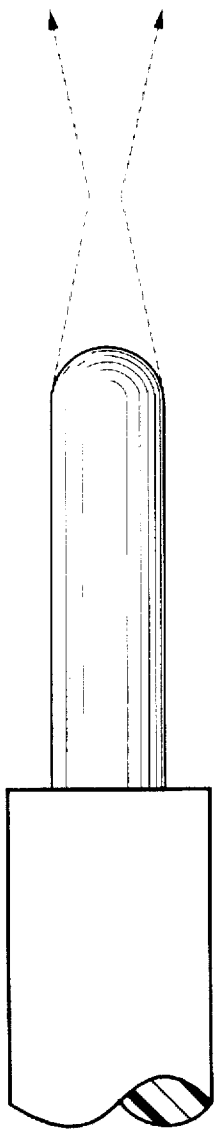
FIG. 7 is an illustration showing the probe attached to the handpiece of the apparatus of FIG. 1 and showing a tubing sleeve for delivering an irrigation fluid to the probe.
Figure 8:
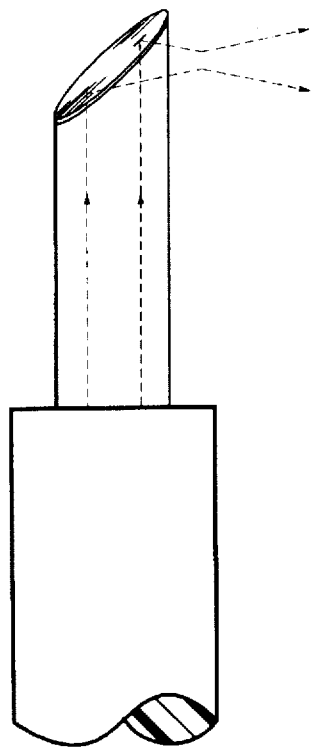
FIG. 8 is an enlarged view in partial cross section of the tubing sleeve and probe illustrated in FIG. 7.

The embodiments of the laser probe 99, 119 illustrated in FIGS. 5 and 6 respectively are preferably used with the improved lens phacoemulsification procedure of the present invention. In the improved lens phacoemulsification method it is also desirable to coaxially deliver irrigation fluid with the laser energy. Referring to FIG. 7, an embodiment of the laser delivery system of FIG. 1 is coupled to a fluid delivery supply. Fluid 192 from the fluid supply is propelled by a pump which is controlled by a foot switch (not shown). A fitting 196 with an entrance port 197 and an exit port 198 is attached over the handpiece 12 and extends just past the exit point of the guide support 22 from the handpiece 12. A flexible plastic tubing 191 extends from a fluid supply into the entrance port 197 of the fitting 196. The fitting 196 is provided to seal the fluid 192 within the space between the fitting 196 and the exterior walls of the handpiece 12. A first piece of PVC tubing 193 overlaps the exit port 198 of the fitting 196 and extends coaxial to the guide support 22 and terminates at the proximal piece 128 of the brass ferule housing 126. The user selects an embodiment of the laser probe that is desired, and slips a second piece of PVC tubing 195 coaxially over the probe. The probe is connected to the guide support 22 by engaging the threads on the proximal piece 128 and distal piece 130 of the brass ferule housing 126. The second piece of PVC tubing 195 that is located coaxial to the laser probe is positioned to overlap the first piece of PVC tubing 193 coaxial to the brass ferule housing 126 thereby connecting the two pieces of tubing and forming a PVC sleeve 190. The fluid 192 travels from the exit port 198 of the fitting 196 through the PVC sleeve 190 and is delivered coaxially with the laser energy. Referring also to FIG. 8, an enlarged view of the laser probe 119, as illustrated in FIGS. 6, is shown within the PVC thin walled sleeve 190. The fluid 192 flows within an annular space 194 that is formed between the probe 119 and the PVC sleeve 190. The second piece of PVC tubing that forms the PVC sleeve 190 terminates just before the microball surface 124 of the silica fiber pigtail to allow an outlet for the fluid at a distal end 195 of the PVC sleeve 190. The fluid upon exiting the PVC sleeve is delivered coaxially to the silica fiber pigtail 120 at the target location. Although discussed in connection with the probe 119, it will be understood that the probe 99 may be similarly adapted to provide coaxial delivery of fluid.

Figure 9:
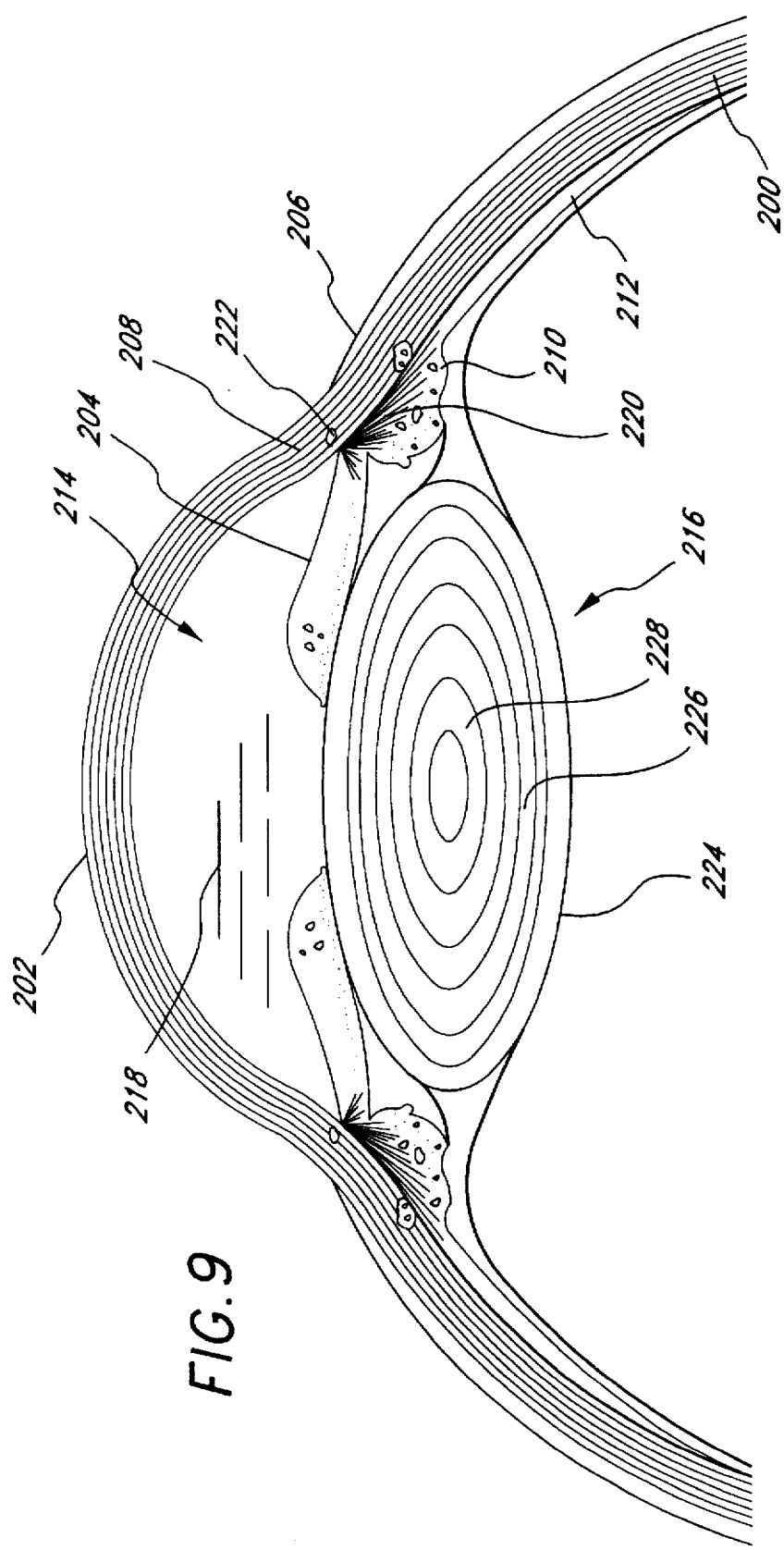
FIG. 9 is a cross-sectional view of the human eye.

Before presenting a description of the phacoemulsification procedures of the present invention, relevant structures of the eye will be described briefly below, as illustrated in FIG. 9, so as to provide background for the anatomical terms incorporated herein, however it should be realized that several anatomical details have been omitted for clarity of understanding. A tough outer membrane known as the sclera 200 surrounds all of the eye except the portion covered by the cornea 202, the thin transparent membrane which covers the iris 204. Outside the sclera 200 is a layer of tissue called conjunctiva 206. The cornea 202 merges with into the sclera 200 at a juncture referred to as the limbus 208. The ciliary body 210 begins at the limbus 208 and extends along the interior of the sclera 200 and becomes the choroid 212. The choroid 212 is the vascular membrane which extends along the retina (not shown) back towards the optic nerve (not shown). The anterior chamber 214 of the eye is the space between the cornea 202 and the lens 216 of the eye which is filled with aqueous humor 218. The trabecular mesh work 220 removes excess aqueous humor 218 from the anterior chamber 214 through Schlemm's canal 222 through veins which merge with blood carrying veins to take the aqueous 218 away from the eye. The crystalline lens 216 of the eye is situated between the iris of the eye 204 and the vitreous body. The lens 216 of the eye is enclosed in a transparent membrane called a lens capsule 224. The lens 216 of the eye is a bi-convex lens that is slightly more concave on the anterior side of the lens. The lens is made up of an outer cortex 226, which is a softer tissue, and a firm central portion, or nucleus 228 of the lens. When a cataract forms, the nucleus 228 becomes quite dense and hard.

Prior to commencing the phacoemulsification procedure of the present invention, a capsulotomy is performed to expose a portion of the lens 216 underlying the lens capsule 224. A preferred apparatus and method for performing a capsulotomy is discussed in co-pending application Ser. No. 680,815, filed Apr. 4, 1991, which is hereby incorporated by reference.

Figure 10:
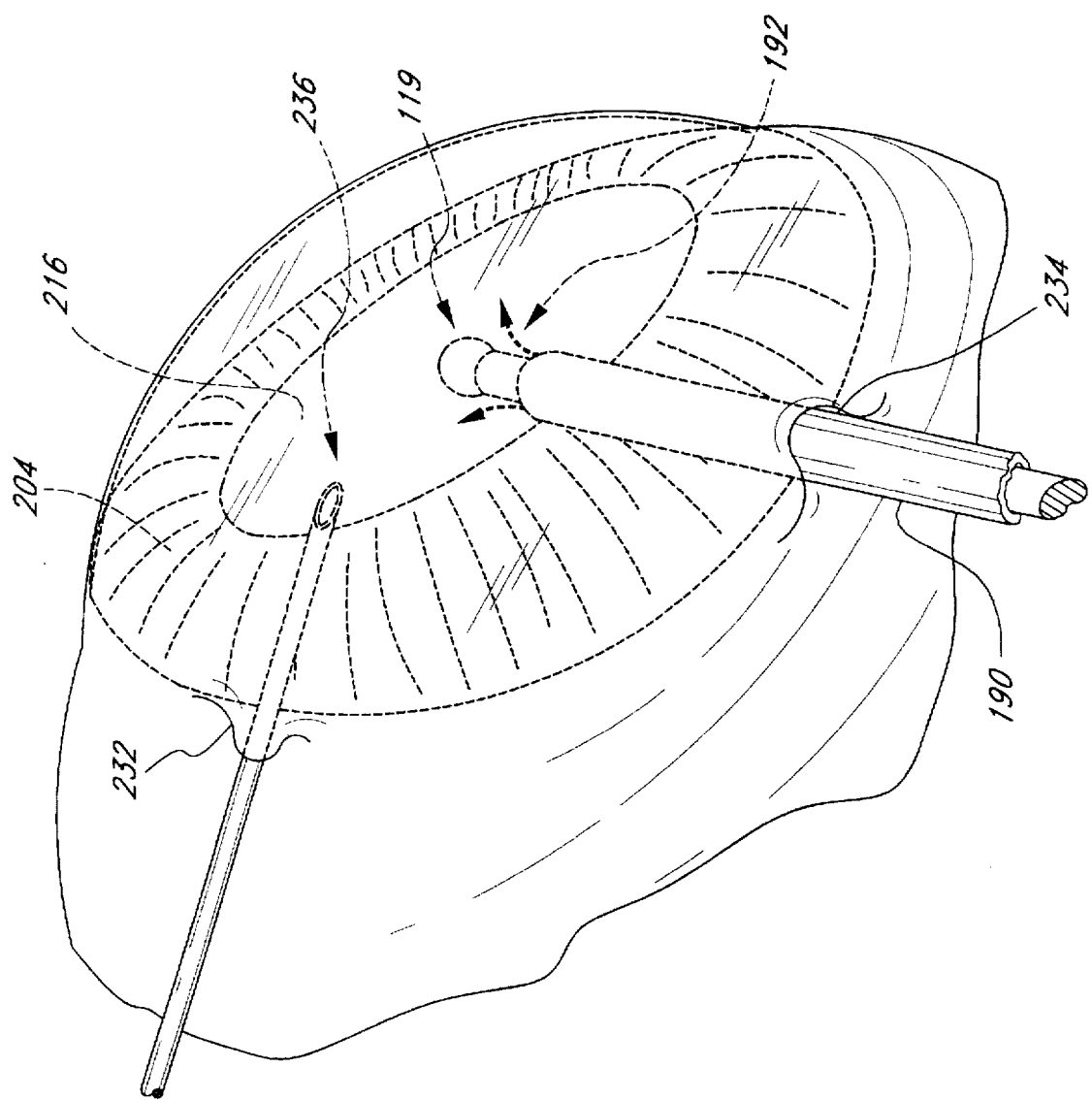
FIG. 10 is an illustration of an eye undergoing the phacoemulsification procedure of the present invention.

Referring to FIG. 10, after performing the capsulotomy, the phacoemulsification procedure is performed using the probe 119 or the probe 99. For convenience, the procedure will be described in connection with the probe 119, however, it will be understood that the probe 99 may be utilized also. Two incisions, a primary incision 234 and a side-port incision 232, are made in either the sclera 200 or the cornea 202 of the eye to allow the entry of instruments into the anterior chamber 214. The laser probe 119 and coaxial PVC sleeve 190 illustrated in FIG. 11 are introduced into the anterior chamber 214 through the primary incision 230. An aspiration probe 236 comprising a 21–23 gauge needle connected to an aspirator is introduced into the anterior chamber 214 through the side port incision 232. The primary incision 234 and side-port incision 232 can be made at any location around the circumference of the anterior chamber 214, or the circumference of the limbus 208.

After the probe has been positioned, optical radiation is directed at the lens 216 of the eye through the laser probe 119 in the form of pulses. The pulses are applied at a repetition rate, a wavelength and an optical energy to simultaneously ablate the lens 216 at the location where the pulses are applied, and to generate shock waves which radiate from the location where the pulses are applied through the nuclear material 228 of the lens 216 to acoustically damage the nuclear material 228 of the lens 216. The application of pulses at the repetition rate, wavelength and optical energy noted above cause significant ablation-induced damage to the lens 216 and significant acoustic-induced damage to the lens 216, whereby the acoustic-induced damage is significantly more widespread than the ablation induced damage. The optical energy at the focal spot is sufficient to cut a crater in the cataractous nuclear material 228 of the lens. The ablation-induced damage of the lens 216 is substantially within the focal spot region while the acoustic-induced damage radiates outwardly from the focal spot and into the nucleus 228 of the lens. The repetition rate may be about 5–25 pulses per second, and in the preferred embodiment, the rate is 10 pulses per second. The energy of each pulse may be about 10–80 mJ, and in the preferred embodiment, the energy of each pulse is about 35 mJ. The duration of each pulse may be about 200 to 300 μsec, and in the preferred embodiment, is 250 μsec. The wavelength of the laser energy used in the preferred embodiment is in the infrared region of the optical spectrum at 2.94 microns.

The spot size at the focal point is between 250 and 350 microns in diameter, and the energy density at the focal spot is 35 to 70 J/cm$^2$. The small spot diameter provides the high energy densities that are required for the lens phacoemulsification procedure of the present invention. In the preferred embodiment, the optical probe 119 generates a focal spot having a diameter of 300 microns with an energy density at the focal spot of about 45 J/cm$^2$. The preferred focal length of the probe (F1) is from 1 to 2 mm and the radius of the micro-ball (RS) is about 0.7 mm, such that the working distance (WD) between the front end surface of the probe and the focal spot is 0.3 to 1.3 mm. In the preferred embodiment the focal length is 1.5 mm, and the working distance (WD) is 0.8 mm. The short focal length of the probe enables delivery of the high density laser energy to the focal point, and causes the excess energy to diverge rapidly beyond the focal point. The energy output from the probe diverges from its end in accordance with a numerical aperture (N.A.) of 0.2, and the focused energy beyond the focal point of the laser probe diverges in accordance with a numerical aperture in the range of 0.3–0.5. This rapid divergence beyond the focal point is advantageous as it reduces the effect of the stray laser energy on the surrounding tissues of the eye that are not being lased, particularly the posterior capsule of the lens.

Typically, the focal spot of the laser optical probe 119 is initially positioned the anterior surface of the cortex of the lens. The soft cortex 226 of the lens quickly emulsifies in response to the laser pulses through ablation alone. As the focal point of the laser is moved deeper into the lens, towards the nucleus 228 of the lens, dense, hard nuclear material is encountered which is significantly less responsive to ablation than the cortex. The focal point of the probe is positioned proximal to epinuclear material, at a location which is substantially at the anterior surface of the nucleus (in some eyes about one-third the original thickness of the lens 216) to form a crater in the nucleus 228 of the lens. As the crater is formed, the pulses of the optical energy generate shock waves in the lens 216 which radiate outwardly from the crater to cause micro-fractures in the cataractous nuclear material 228 of the lens, thereby causing the acoustically-induced damage outside the focal spot. The micro-fractured nuclear material is sufficiently reactive to the pulses of optical energy to cause the nuclear material 228 to readily disintegrate upon exposure to the focal spot of the optical energy. The optical probe 119 is moved along a path across the nuclear material 228 over the entire surface of the lens to "paint" the lens with the laser energy at a sufficiently slow rate to cause ablation of the lens material and form craters in the nucleus at multiple locations along the path. The ablation forcibly dislodges microscopic particles of lens tissue which produces the viscous milky fluid. When the focal spot of the optical energy is placed on acoustically-damaged material, the lens material disintegrates into small fragments. In effect, the lens "falls apart," creating fragments at least about an order of magnitude smaller in size than the original lens, and commonly no larger than the focal spot. These fragments mix with the milky fluid to form an emulsion which can be removed by aspiration through a 500 micron diameter aspiration probe.

It is preferable that, during the above described process, the laser probe 119 is moved across the lens so as to prevent the lens from fracturing into large pieces. If the probe is held in a single location (e.g., at the middle of the lens) too long, the lens may divide into large pieces. If this occurs, the pieces may be held in a stable location by the aspiration probe, using the suction from the probe to draw the piece against the aspiration port in a manner similar to that used in ultrasonic emulsification techniques, and laser pulses are applied to emulsify each piece. By moving the probe 119 to multiple locations on the lens, and lasing a short time at each location, the unemulsified portion of the lens will remain as a unitary whole until the removal process is substantially completed. This procedure advantageously eliminates the need to manipulate multiple chunks of lens and enhances the efficiency of the lens removal technique.

During the lasing process, irrigation fluid 192 is preferably constantly supplied through the primary incision 234 into the anterior chamber 214 of the eye to remove heat that may be generated during the emulsification process. The fluid flows through the annular area 194 between the coaxial PVC sleeve 190 and the probe 119. The fluid 192 is preferably a Balanced Salt Solution (B.S.S.) which is close in composition to the solution Of the aqueous humor 218 of the eye. Preferably, the application of fluid 192 is simultaneous to the application of the aspiration through the aspiration probe 236 in the side-port 232 to maintain the proper pressure within the anterior chamber 214 of the eye. This process helps to maintain the proper anatomical relationships of the structures within the eye during lasing. In addition to removing the excess fluid 192 from the anterior chamber 214 of the eye, the aspiration probe 236 is used to remove the emulsified lens tissue from the anterior chamber 214. The milky fluid and the small debris suspended therein can be readily drawn through the port in the end of the aspiration probe 236. Although it is usually preferable that irrigation and the aspiration occur concurrently with application of the laser energy, either irrigation or aspiration or both may be interrupted for short intervals during lasing. By utilizing the side-port incision 232 for aspiration, fluid may advantageously be drawn across the surface of the probe to wash lased material off the tip of the probe. This method of aspiration also permits emulsion to be drawn away from the path of the laser energy, at an angle thereto, thus minimizing the possibility of relasing tissue that has already been emulsified. By constantly introducing cool irrigation fluids 192, such as B.S.S., to the anterior chamber 214, and by removing the heated lased debris and fluid, the heating of the intraocular structure is reduced. In addition, the passage of fluid 192 over the tip helps to keep the tip of the optical probe 119 cool, and minimizes the effects of thermal damage to the probe 119.

Another advantage of aspirating through a side-port incision 232 rather than the primary incision 234 is that it permits the size of the primary incision 234 to be reduced. Because the aspiration probe 236 is separate from the laser probe 119, the laser probe can be of a smaller diameter, and the incision through which the laser probe is inserted can also be smaller, such that it can be closed with minor suturing or with no suturing. The reduced size of the primary incision allows the surgeon to take advantage of existing and advancing technologies with regard to small incision intraocular lenses to replace the emulsified lens. In addition, the smaller incision allows for more rapid visualization, and less astigmatism as a result of the surgical procedure. Further, the size of the side-port incision 232 is small enough that it can be self-healing and does not require suturing. Also, a separate aspiration probe and side-port incision allows the surgeon to use the aspiration probe 236 to manipulate intraocular tissue during lasing, or mechanically stabilize the eye to prevent movement thereof while lasing is occurring through the primary incision 234.

After the nucleus 228 has been emulsified by the laser radiation, the aspiration probe 236 is used to remove any remnants of soft cortical tissue and emulsified material, as well as to vacuum the material surface of the lens capsule. During such removal and vacuuming, irrigation fluid is supplied through the laser probe 119. Thereafter, both probes 119, 236 are removed from the eye, and an irrigation sleeve is placed on the aspiration probe 236 to supply irrigation fluid circumferentially (i.e., coaxially) around the aspiration probe. The aspiration probe 236 is then inserted into the eye through the primary incision 234 and any remnants of soft cortical tissue and emulsified material are removed from any remaining o'clock positions which could not be reached through the side port 232. Additionally, the internal surface of the lens capsule is again vacuumed such that all debris is removed from the eye. Irrigation fluid is supplied through the irrigation sleeve on the aspiration probe 236 during such removal and vacuuming.

What is claimed is:

1. A method of removing a lens of an eye, comprising:

(a) inserting a probe into the anterior chamber of said eye;

(b) directing pulses of laser radiation from said probe against a location on nuclear material of said lens;

(c) selecting the wavelength, repetition rate and pulse energy of said laser radiation such that during step (b), said pulses simultaneously (1) ablate said lens within an ablation zone, and (2) generate shock waves which radiate from said location and propagate through said nuclear material so as to cause substantial acoustic damage thereto, said damage being in an acoustic zone that extends outside said ablation zone into at least a substantial portion of said nuclear material;

(d) moving said probe such that said pulses of laser radiation are directed onto acoustically damaged nuclear material, whereby said simultaneous ablation and shock wave generation readily transform said nuclear material into an emulsion capable of aspiration; and (e) aspirating said emulsion from said eye.

2. The method of claim 1, wherein step (b) comprises the step of focusing said lens radiation at a focal spot within said nuclear material of said lens, and wherein step (b) comprises the step of moving said focal spot along a path within said nuclear material sufficiently slowly to cause ablation at multiple locations along said path.

3. The method of claim 2, wherein said focal spot is no more than a few hundred microns in diameter, and wherein step (b) comprises moving said focal spot across substantially the entire lens.

4. The method of claim 1, wherein said wavelength is in a mid-infrared wavelength region and on the order of 3 microns, and wherein said pulse energy is 10–80 mJ per pulse.

5. The method of claim 1, wherein step (b) comprises ablating a crater in said lens.

6. The method of claim 5, wherein said crater is in said nuclear material.

* * * * *